United States Patent
Esch et al.

(10) Patent No.: US 6,836,374 B2
(45) Date of Patent: Dec. 28, 2004

(54) LENS SYSTEM AND METHODS FOR POWER ADJUSTMENT

(75) Inventors: Victor Esch, Albuquerque, NM (US); John H. Shadduck, Tiburon, CA (US)

(73) Assignee: PowerVision, Inc., San Francisco, CA (US)

( * ) Notice: Subject to any disclaimer, the term of this patent is extended or adjusted under 35 U.S.C. 154(b) by 0 days.

(21) Appl. No.: 10/717,832

(22) Filed: Nov. 19, 2003

(65) Prior Publication Data

US 2004/0169932 A1 Sep. 2, 2004

Related U.S. Application Data

(60) Provisional application No. 60/428,173, filed on Nov. 20, 2002.

(51) Int. Cl.⁷ .................................................. G02B 1/06
(52) U.S. Cl. ...................................... 359/665; 359/666
(58) Field of Search .................................. 359/665, 666

(56) References Cited

U.S. PATENT DOCUMENTS

| | | | |
|---|---|---|---|
| 4,787,903 A | 11/1988 | Grendahl | |
| 4,816,031 A | 3/1989 | Pfoff | |
| 5,066,301 A | 11/1991 | Wiley | |
| 5,288,293 A | 2/1994 | O'Donnell, Jr. | |
| 5,443,506 A | 8/1995 | Garabet | |
| 5,774,273 A | 6/1998 | Bornhorst | |
| 6,124,980 A | 9/2000 | Cerbell | |
| 6,188,526 B1 | 2/2001 | Sasaya et al. | |
| 6,195,807 B1 * | 3/2001 | Chou | 2/428 |
| 6,493,151 B2 * | 12/2002 | Schachar | 359/666 |
| 6,552,860 B1 * | 4/2003 | Alden | 359/742 |
| 2004/0001180 A1 * | 1/2004 | Epstein | 351/159 |
| 2004/0008419 A1 * | 1/2004 | Schachar | 359/666 |

* cited by examiner

*Primary Examiner*—Evelyn A. Lester
(74) *Attorney, Agent, or Firm*—Nicola A. Pisano, Esq.; Luce, Forward, Hamilton & Scripps LLP

(57) ABSTRACT

A lens is provided that having optical parameters that may be adjusted in-situ, and is particularly useful as an IOL for use in cataract patients that require an adjustment in the optical power of the lens post-implantation. In one embodiment, the lens body carries an array of interior fluid-filled cells in which fluid is controllably moved upon application of energy from an external source to move a fluid media into or out of the cells to thereby alter the lens surface shape.

29 Claims, 8 Drawing Sheets

LENS SYSTEM AND METHODS FOR POWER ADJUSTMENT

REFERENCE TO RELATED APPLICATIONS

This application claims the benefit of priority from U.S. provisional application 60/428,173, filed Nov. 20, 2002 titled "Lens System and Method for Power Adjustment".

FIELD OF THE INVENTION

The present invention relates to lenses having optical parameters that are adjustable in-situ. More particularly, the invention has applications in IOLs for in-capsule implantation for cataract patients, and in contact lenses, wherein an external energy source is applied to the lens to control movement of fluid media within interior cells of the lens, thereby altering the lens curvature to correct aberrations.

BACKGROUND OF THE INVENTION

Cataracts are a major cause of blindness in the world and the most prevalent ocular disease. Visual disability from cataracts accounts for more than 8 million physician office visits per year. When the disability from cataracts affects or alters an individual's activities of daily living, surgical lens removal with intraocular lens (IOL) implantation is the preferred method of treating the functional limitations. In the United States, about 2.5 million cataract surgical procedures are performed annually, making it the most common surgery for Americans over the age of 65. About 97 percent of cataract surgery patients receive intraocular lens implants, with the annual costs for cataract surgery and associated care in the United States being upwards of $4 billion.

A cataract is any opacity of a patient's lens, whether it is a localized opacity or a diffuse general loss of transparency. To be clinically significant, however, the cataract must cause a significant reduction in visual acuity or a functional impairment. A cataract occurs as a result of aging or secondary to hereditary factors, trauma, inflammation, metabolic or nutritional disorders, or radiation. Age related cataract conditions are the most common.

In treating a cataract, the surgeon removes the crystalline lens matrix from the lens capsule and replaces it with an intraocular lens ("IOL") implant. The typical IOL provides a selected focal length that allows the patient to have fairly good distance vision. Since the lens can no longer accommodate, the patient typically needs glasses for reading. The surgeon selects the power of the IOL based on analysis of refractive characteristics of the patient's eye prior to the surgery. However, in a significant number of cases, after the patient's eye has healed from the cataract surgery, there is a refractive error that could not be predicted. It is quite common for residual errors after IOL implantation to occur, and in fact, such errors may occur in the vast majority of IOL patients. This error reportedly averages approximately 0.6 diopters, with a +/−0.5 standard deviation. Thus, many patients experience an error of over 1.0 diopter.

Various types of methods and apparatus have been proposed for altering the corrective power of an ophthalmic lens in-situ. For example, U.S. Pat. No. 6,450,642 to Jethmalani et al. describes a lens that is capable of post-fabrication power adjustment. Specifically, a partially polymerized polymer lens matrix is described that is capable of stimulus-induced further polymerization to permanently alter the lens in a selected shape.

U.S. Pat. No. 5,443,506 to Garabet describes a fluid-filled lens wherein the focusing power may be altered by changing the index of refraction of fluid carried within a central optic portion. U.S. Pat. No. 5,066,301 to Wiley describes an IOL having a fluid-filled or gel-filled lens that carries a plurality of light-reflective particles, wherein the orientation of the particles is controlled by an electromagnetic field to thereby alter the spherical power of the lens. In another similar approach, U.S. Pat. No. 4,787,903 to Grendahl discloses a fresnel-type IOL with an overlying layer of a liquid crystalline composition that has a variable index of refraction depending upon its stimulation by electrical or light energy to provide a post-implant adjustability.

U.S. Pat. No. 4,816,031 to Pfoff discloses an IOL with a hard PMMA lens separated by a single chamber from a flexible thin lens layer. The lens assembly is adjusted by microfluid pumps that vary a volume of fluid between the PMMA lens portion and the thin layer portion. U.S. Pat. No. 5,288,293 to O'Donnell discloses an intraocular lens comprising a plurality of layers of materials that respond to the application of laser energy to form microfenestrations that alter the anterior lens curvature.

Although previously known workers in the field of in-situ adjustable lenses have made some progress, the relative complexity of the methods and apparatus developed to date have prevented widespread commercialization of such devices. Moreover, previously known methods and apparatus have been directed to in-situ modifications that attempt to alter the lens axial position within the eye or overall curvature of the lens. However, such gross modifications to lens position or curvature are limited by materials and space constraints.

In view of the foregoing, it would be desirable to develop in-situ adjustable lenses that overcome the drawbacks of previously known devices. It would therefore be desirable to provide apparatus and methods that enable localized modification of the surface of a lens to correct errors, such as defocus error. This may be commonly thought of as moving the focus of the IOL system to the retina, and may be effected by actual axial motion and/or modification of the surface of the IOL, e.g., by changing the radius of curvature of one or more of the surfaces of the IOL.

In addition to modifying the placement of the focal point at the retina, it would be desirable to provide methods and apparatus that permit in-situ localized correction of other aberration properties of the eye, for example astigmatism of the eye, which may be associated with the cornea, or to correct higher order aberrations to improve visual acuity.

It also would be advantageous to provide methods and apparatus for manipulating the surface of an IOL on a localized basis after the IOL has been implanted and the access incision has healed. In order to provide such in-situ modification of the IOL surface, it would be desirable to provide an IOL configured to be modified by application of energy from a remote source, such as a laser, radio-frequency energy or ultrasonically.

It still further would be desirable to provide methods and apparatus for manipulating the surface of a lens in-situ, wherein the application of energy from an external source is performed in cooperation with a wavefront sensor system, so as to permit optimization of localized correction of the lens.

SUMMARY OF THE INVENTION

In view of the foregoing, it is an object of the present invention to provide apparatus and methods that enable localized in-situ modification of the surface of a lens to correct errors, such as defocus error, astigmatism and higher order aberrations.

It is also an object of this invention to provide apparatus and methods that enable localized in-situ modification of the surface of a lens to not only restore loss of sight due to cataracts, but which actually improve visual acuity.

It is another object of the present invention to provide methods and apparatus for manipulating the surface of an IOL on a localized basis after the IOL has been implanted and the access incision has healed.

It is a further object of the present invention to provide methods and apparatus for in-situ localized modification of the lens surface by application of energy from a remote source, such as a laser, radio-frequency energy, chemically or ultrasonically.

It is another object of this invention to provide methods and apparatus for manipulating the surface of a lens in-situ wherein the application of energy from an external source is performed in cooperation with a wavefront sensor system, so as to permit optimization of localized correction of the lens.

These and other objects of the present invention are accomplished by providing a lens including an optic element comprising resilient, locally-deformable anterior and posterior polymer elements sandwiched against an array of deformable cells. The array of deformable cells is index-matched to the anterior and posterior elements and may be surrounded by a fluid that also is index-matched with the polymer of the lens. Each of the deformable cells in turn defines a secondary fluid-filled chamber having an adjustable interior fluid volume, so that changes in the volume of the deformable cells result in corresponding localized deformation of surfaces of the anterior and/or posterior elements.

The deformable cells generally are adapted to be moved controllably between a retracted position and an axially-extended position to engage and controllably deform the anterior and/or posterior lens element upon the application of energy from an external energy source, such as a laser source. The number of cells may vary from as few as one to more than 250, and preferably are individually controllable using an external power source. The lens of the invention thus allows for a post-implant power adjustment of an IOL with an inexpensive low power laser source.

In accordance with the present invention, a selected number of deformable cells, or even a single cell, may be adjusted to alter a local region of the anterior and/or posterior lens surface, for example to correct an astigmatism or higher order aberration. Alternatively, the deformable cells within a region may be moved controllably to an axially extended position to alter the anterior and/or posterior lens surface globally to correct the sphere of the lens.

In accordance with one aspect of the present invention, an exemplary lens provides paired fluid inflow and outflow channels that communicate with each fluid-filled cell. Further, a non-optic portion of the lens carries a reservoir system that is coupled to the inflow and outflow channels by flow control mechanisms, such as one-way valves or sacrificial plugs, that allow flows of fluid to and/or from the reservoir system under the application of energy from an external source, such as from a laser source. Depending upon the specific flow control mechanisms employed in the lens, power adjustment of the lens may be performed on a one-time basis or may be periodically repeated post-implant over the lifetime of the patient.

In accordance with another aspect of this invention, the external source that targets and addresses the flow control mechanisms within the IOL may be under the control of a wavefront sensor system, thus allowing for intraoperative lens power calculations while adjusting the lens power.

According to yet another aspect of this invention, a contact lens constructed as described above may be adjusted in-situ in a patient's eye using an external energy source and a wavefront sensor system to optimize visual acuity achievable with the lens.

Methods of using and adjusting the lens of the present invention also are provided.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention is directed to an in-situ adjustable lens system, with particular applicability in the fields of implantable intraocular lenses ("IOLs") and custom contact lenses. As will be described below, the system of the invention also may be utilized to adjust the power of other types of lenses used for vision correction, for example phakic IOLs and contact lenses. For convenience, the system is first described in the context of exemplary in-the-capsule IOLs.

In accordance with the principles of the present invention, methods and apparatus are provided wherein a lens has a locally deformable surface coupled to a one or more independently actuable fluid-filled actuators or cells. The volume within, and deformation of, the fluid-filled cells is controlled by selective actuation, using an external power source, of individual flow control mechanisms coupled between the cells and one or more reservoirs.

Subsequent to implantation of the IOL and healing of the access incision, the IOL would approximate the appropriate power for the individual eye; the optical path difference ("OPD") of the lens then may be adjusted to optimize the optical performance in-situ. As described herein below, the net effect of modifying each cell element, each and in concert, is to provide for the improvement of the optical performance of the optical system, for example the human eye, in which the lens element is placed. By the proper choice of the extent of displacement of the cell or actuator, either increasing the OPD or decreasing it, the IOL may be made to cancel all or a substantial portion of the optical imperfection associated imaging system. Thus, an incoming wavefront from the cornea will impinge upon the IOL, and the aberrated wavefront can be substantially compared to ideal spherical wavefront. The individual cells or actuators then can be modified to impart the appropriate OPD upon the wavefront such that at the wavefront is substantially perfect after transmission through the lens.

Figure 1A:
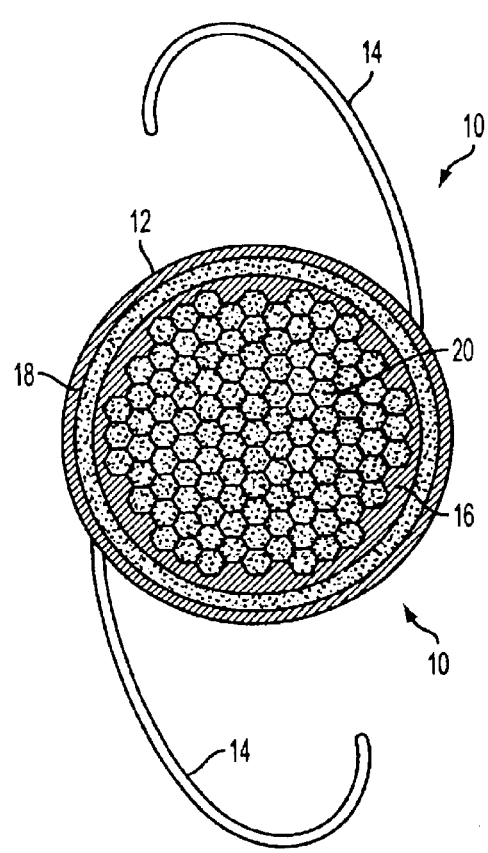
FIGS. 1A–1C are, respectively, front and side views of an exemplary embodiment of an intraocular lens constructed in accordance with the principles of the present invention.

Referring to FIG. 1, exemplary intraocular lens 10 constructed in accordance with the present invention is described. As is conventional for intraocular lenses, lens 10 includes lens portion 12 and haptics 14. As for conventional IOLs, the diameter of outermost portions of haptic portions 14 typically is about 13.0 mm while and the diameter of lens portion 10 is about 5.0 mm to 8.0 mm.

Figure 1B:
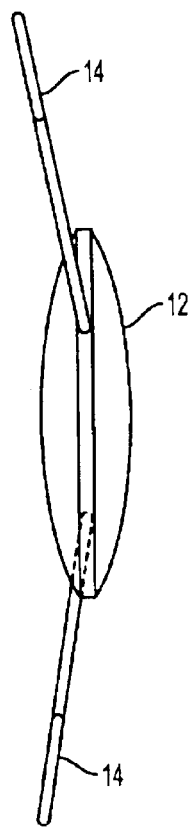
Figure 1C:
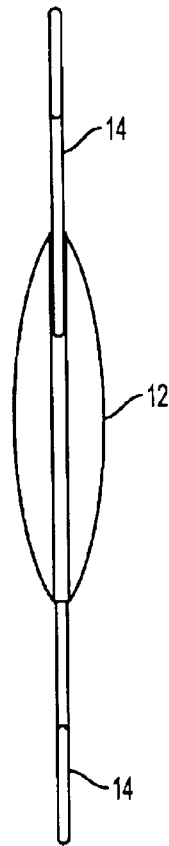

Haptic portions 14 may be of any suitable configuration known in the art, and illustratively comprise two opposing flexible elements that have radial-outward ends that define arcuate terminal portions to create a slight engagement pressure when in contact with the perimeter of the capsular sac. In the embodiment of FIG. 1B, haptic portions 14 are disposed at an angle with respect to the plane of lens portion 10, while in FIG. 1C haptic portions 14 are aligned in the plane of the lens portions.

Lens portion 12 includes central optic portion 16 through which light is refracted onto the optic nerve, and support region 18, which supports haptics 14 and in addition houses non-optical portions of the adjustment system for central optic portion 16. As depicted in the exemplary embodiment of FIG. 1A, central optic portion 16 includes an array of deformable cells 20, illustratively in the form of fluid-filled hexagonal chambers. Deformable cells 20 are coupled to the anterior and posterior resilient polymer members, so that selectively adjustment of an axial dimension of deformable cells 20 causes either localized or global adjustments to the optical parameters of the central optic portion. As described in further detail hereinbelow, adjustment of the axial dimension of deformable cells 20 may be accomplished in response to energy delivery from a remote source, for example from a laser source.

Figure 2A:
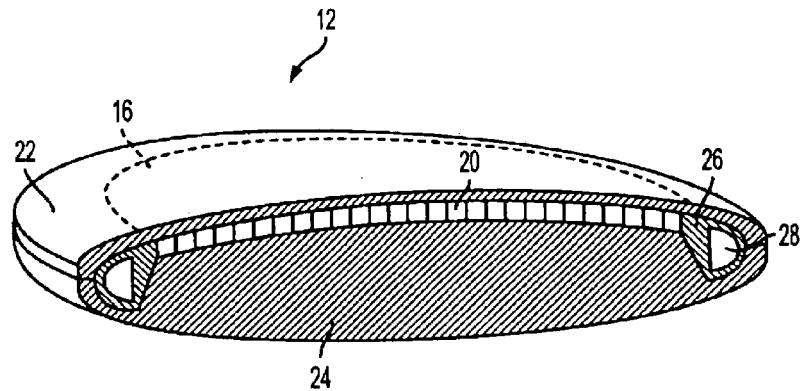
FIGS. 2A and 2B are, respectively, perspective and exploded perspective views of the non-haptic portion of intraocular lens of FIGS. 1A–1C.
Figure 2B:
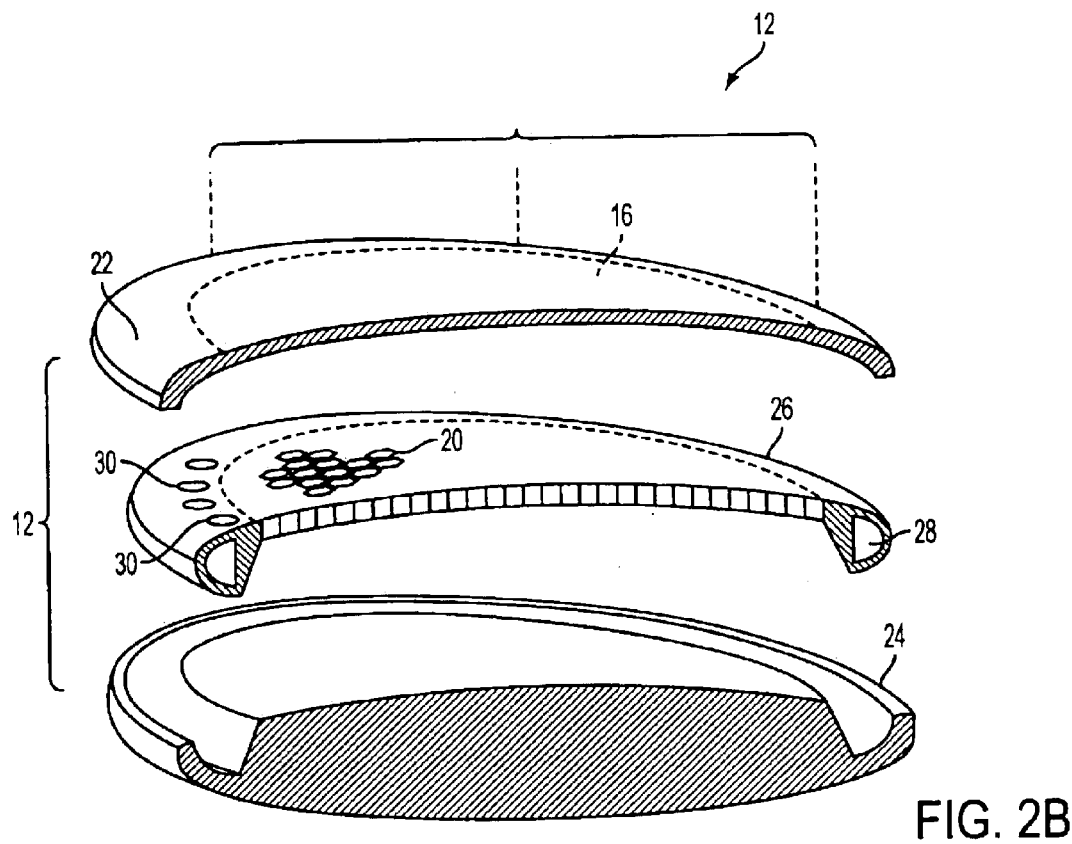

Referring now also to FIGS. 2A and 2B, lens portion 12 comprises anterior element 22 and posterior element 24 that are sandwiched against central element 26. Central element 26 includes array of deformable cells 20 and one or more reservoirs 28 disposed at the periphery of central element 26. Each of elements 22, 24 and array of cells 26, may be made of a transparent flexible, deformable material, such as silicone polymeric material, acrylic polymeric material, hydrogel polymeric material or the like, all of which allow the lens to be rolled or folded for carrying in the lumen of a small diameter introducer for subsequent deployment into the eye through a small incision. As will be described below, the functionality of the lens depends on the degree of flexibility of at least one of the anterior and posterior elements.

Alternatively, at least one of anterior or posterior elements 22 and 24 may be fabricated of a slightly stiffer biocompatible material, if very thin in cross section, such as polymethyl methacrylate (PMMA). In this case, lens portion 16 may be formed of different materials such as silicons and PMMA. Preferably, the array of cells 26 and elements 22 and 24 may be formed using injection-molding. Alternatively, elements 22 and 24 may be fabricated using turning or casting techniques known in the art. The choice of materials may be further informed by the requirements of mechanical properties, temperature sensitivity, optical properties such as dispersion, moldability properties, and so on.

Figure 3:
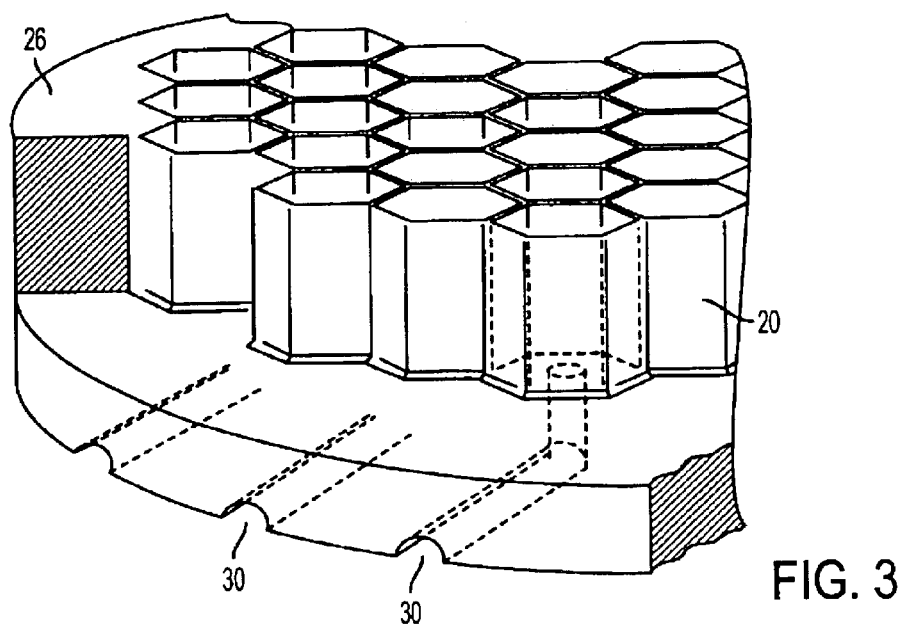
FIG. 3 is a partial perspective view of the array of deformable cells disposed within the middle layer of the lens of FIG. 2B.

Referring now also to FIG. 3, deformable cells 20 may be arranged in the form of a hexagonal honeycomb, wherein each cell 20 of the array is coupled to one or more reservoirs 28 by one or more channels 30. Each channel 30 includes a flow control mechanism, such as a sacrificial plug of polymer or wax-like material or a one-way or two-way valve, that is actuable using an external energy source.

In accordance with the principles of the present invention, correction of defocus error and other aberrations may be addressed by the actuation and axial displacement of the surface of anterior or posterior elements at or about several localized paths. The deformable cell 20 underlying a targeted location of central optic portion 16 may be altered in dimension by fluid flows to or from reservoirs 28 to increase or decrease the optical path along through the cell and the adjoining portions of the anterior and posterior elements 22 and 24. Each of several regions of central optical portion 16 may be modified, either increasing or decreasing the optical path experienced by traversing the IOL at that location, as needed to correct the defocus error or other aberration.

In general, deformable cells 20 each actuate in a dimension substantially axial to the optic axis of the IOL, and may be addressed in groups or individually. Cells 20 are actuated through the addition of, or subtraction of, index-matched fluid media M from the cell. The control of this fluid M may be locally, from or to reservoir 28 via a flow control mechanism located within the optical portion 16 of the IOL. Alternatively, the fluid may be controlled to flow to and from cells 20 to or from reservoir 28 via flow control mechanisms located within support portion 18 of lens portion 12, outside of the optical path of light traversing the IOL. Each cell 20 is supplied through one or more channels 30, wherein the fluid is index-matched to the other components of the lens.

Fluid media M is selected so that it is index-matched to the material of deformable cells 20 and adjoining surfaces that might otherwise cause unwanted phase errors or diffractive effects. Silicones are examples of materials that are obtainable with equal index of refraction in both the liquid and solid state. Other materials may be chosen to match the index, using liquid silicones and solid PMMA, for example, or solid silicones and water solutions, or water. Thus the desired effect of index matching may be achieved so as to render the solid structure undetectable in the visible region of the spectrum.

Figure 4A:
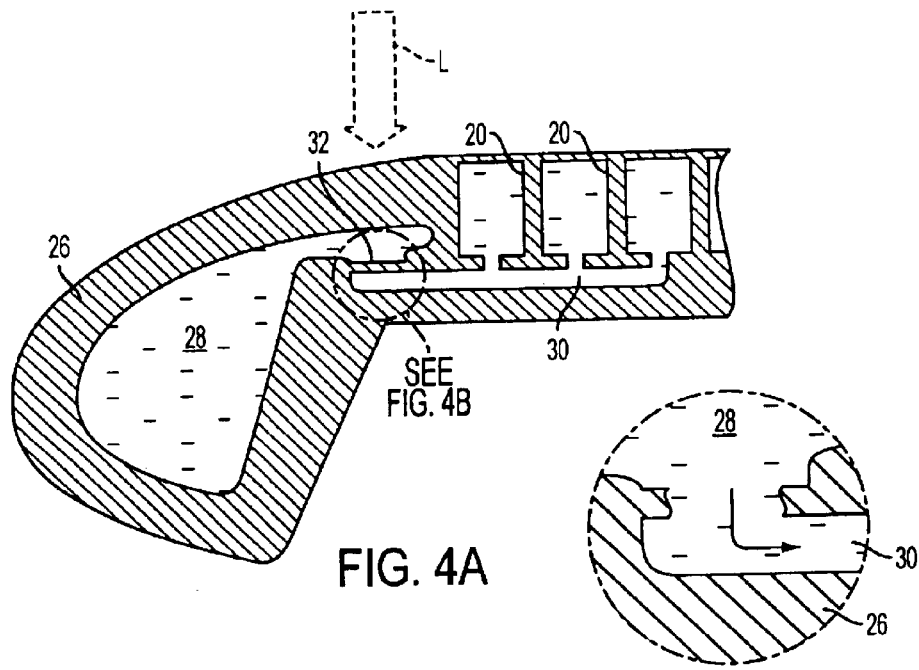
FIGS. 4A and 4B are, respectively, schematic sectional views of a sacrificial plug disposed between the inflow and/or outflow channels of the deformable cells and a reservoir in the non-haptic portion of the lens of FIG. 2B, in sealed and opened positions.
Figure 4B:
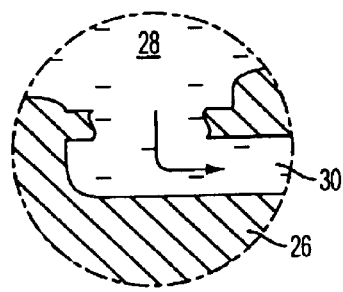

Referring again to the exemplary embodiment depicted in FIG. 2B, flow control mechanisms 30, which couple groups of cells 20 to reservoir 28, may be disposed in a ring-like arrangement on the periphery of central element 26, between channels 30 and reservoirs 28. As illustrated in FIGS. 4A and 4B, flow control mechanisms comprise sacrificial plugs 32 formed from locally thinner regions of the substrate material of central element 26, and couple reservoir 28 to a group of cells 20. The substrate material of central element 26 within the locally thinned region may in addition include a suitable dopant to facilitate heat-up and melting of plug 32.

When exposed to beam L of laser light of a predetermined wavelength, plugs 32 melt, thereby permitting higher pressure in the corresponding reservoir 28 to be communicated through channels 30 to a group of deformable cells 20, as indicated by the arrow in FIG. 4B. The resulting increased pressure in deformable cells 20 causes axial extension of the cells in that group. This dimensional change manifests as a localized variation in the curvature of the overlying portions of one or both of anterior element 22 and posterior element 24. It should be of course understood that each of cells 20 and channel 30 contains fluid that is indexed-matched to the material of central element 26, so that removal of plug 32 merely increases the static pressure in the cells that are joined to reservoir 28 upon opening of the plug.

Figure 5A:
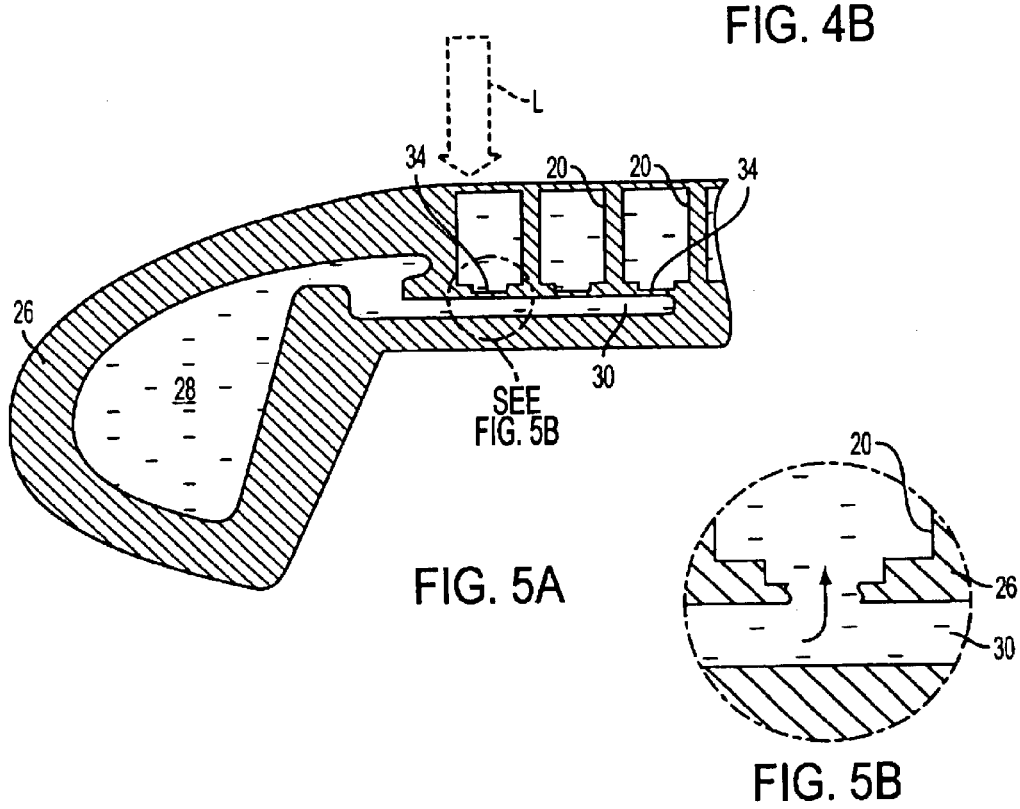
FIGS. 5A and 5B are, respectively, schematic sectional views of sacrificial plugs disposed between the inflow and/or outflow channel and individual deformable, in sealed and opened positions.
Figure 5B:
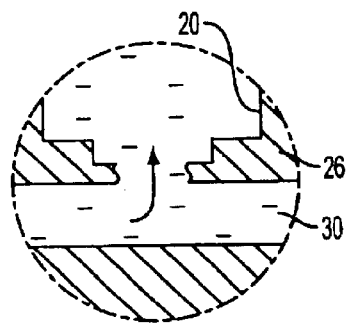

Alternately, as depicted in the exemplary embodiment of FIGS. 5A and 5B, flow control mechanisms comprise sacrificial plugs 34 formed from locally thinner regions of the substrate material of central element 26 at the base of each of cells 20. Plugs 34 individually couple cells 20 to a higher (or lower) static pressure maintained in channel 30, which in turn communicates with reservoir 28. As for the embodiment of FIG. 4, the material forming plugs 34 may include a suitable dopant to facilitate heat-up and melting of the plug.

When exposed to beam L of laser light of a predetermined wavelength, plug 34 melts, thereby permitting higher (or lower) pressure in the channel 30 corresponding to be communicated from reservoir 28 to the interior of a single deformable cell 20, as indicated by the arrow in FIG. 5B. The resulting pressure change in deformable cell 20 causes a change in the axial dimension of the cell, which again manifests as a localized variation in the curvature of the overlying portions of one or both of anterior element 22 and posterior element 24. As should be appreciated, the extent to which the localized variation appears in either the anterior or posterior elements is a function of the relative stiffness of these components.

As should be appreciated, the index-matched fluid in reservoir 28 may maintain a higher or lower static pressure than the fluid in cells 20, as may be desirable for a specific region or group of cells, depending upon its location in central optic portion 20. Thus, for example it may be desirable to manufacture central portion 26 with a central-most group of cells 20 at a higher pressure than those on the periphery, or vice-versa, and to provide reservoirs 28 of differing static pressures, to accentuate the range of localized variations of curvature achieved across the surface of the lens.

In addition, care must be taken to ensure that individual cells 20 do not work independently, to minimize the creation of discontinuities between adjacent cells. Such discontinuities may cause diffraction effects that are undesirable in any imaging system, but particularly in the sensitive vision system of humans. Accordingly, cells 20 should be coupled mechanically, for example through a planar portion of central element 26 that is substantially perpendicular to the optical axis.

Fluid manipulation and control may be through several methods appropriate to the external transmission of energy to the IOL to move fluid media M. As described above, lasers 100 and 110 are expected to be particularly advantageous to provide usable power to actuate flow control mechanisms 32 and 34. In addition, other forms of flow control mechanisms may be employed, including active pumping mechanisms that rely upon thermal phenomena, such as thermal expansion, bi-stable metallic or plastic elements, phase transition or swelling of materials, photo activation of polymers, and so on.

Instead of active pumping mechanisms, flow control mechanisms suitable for use with the lens of the present invention may employ photo-activated valves, whether thermo-mechanical, electro-mechanical, electromagnetic, fluid-magnetic, or any other appropriate valve system known in the art that may be activated externally, in order to allow flows of media. Thus, a high-pressure reservoir may reside external to central optical portion 16, and flow may be controlled into cells 20 using a laser-actuated valve. Preferably, the valve also would be located outside the central optic portion 16.

Alternatively, an out-flow valve may be used that allows fluid to flow out of cells 20, thus controlling the amount of fluid within the cell. In this latter case, the fluid within cell 20 would be at a higher pressure than the accepting reservoir, and the IOL would be implanted with all cells extended to near their full travel. In this manner, aberrations of the eye then may be corrected by the appropriate removal of fluid from individual cells as needed to provide the necessary correction.

As described hereinabove, the movement of fluid may be accomplished using flow control mechanisms that mediate pressure differentials between the interiors of cells 20 and one or more reservoirs 28 of higher or lower pressure. For example, two reservoirs may be employed such that the relation $P_{fill} > P_{cell} > P_{empty}$ is maintained throughout the full dynamic range of the cells that is required to provide proper correction of the performance of the optical system, such as the human eye, wherein $P_{fill}$ is the pressure of the high pressure reservoir, $P_{cell}$ is the pressure within cells 20, and $P_{empty}$ is the pressure within the lower pressure reservoir.

In accordance with yet another aspect of the present invention, it may be desirable to seal channels 30 when a desired degree of modification of the lens surface has been attained, for example, by terminating pumping process or using a photo-curing or cross-linking effect, etc. Alternatively or in addition, it also may be desirable to cure the entirety of lens portion 12 after a desired degree of correction has been achieved through photo-polymerization of the fluid material. Silicones are a class of materials that may be photo-polymerized, typically using blue light; other polymers exist that exhibit this effect.

Figure 6A:
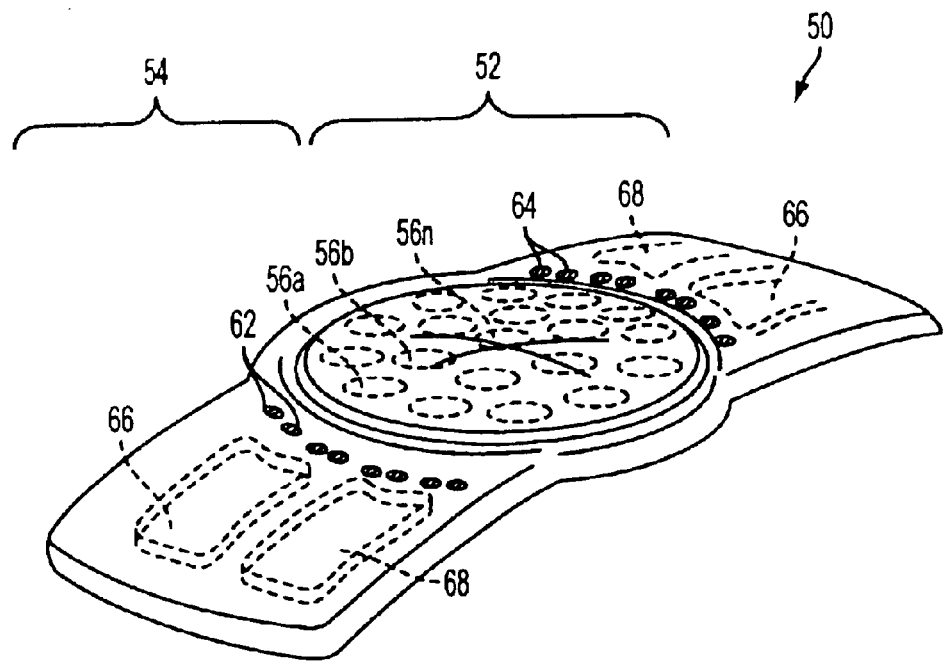
FIGS. 6A and 6B are, respectively, perspective and plan views of an alternative embodiment of an intraocular lens of the present invention.
Figure 6B:
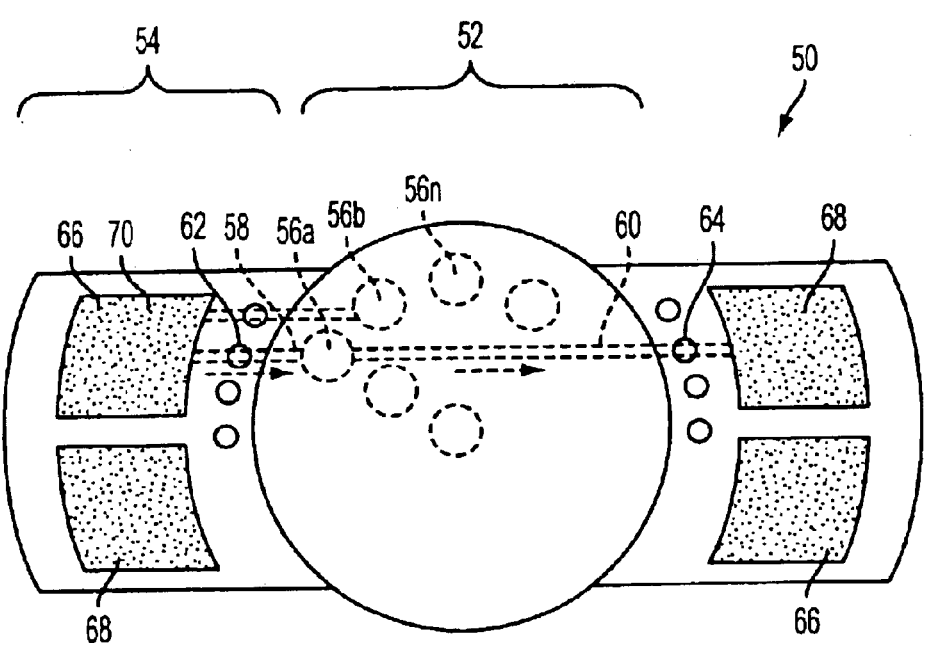
Figure 7A:
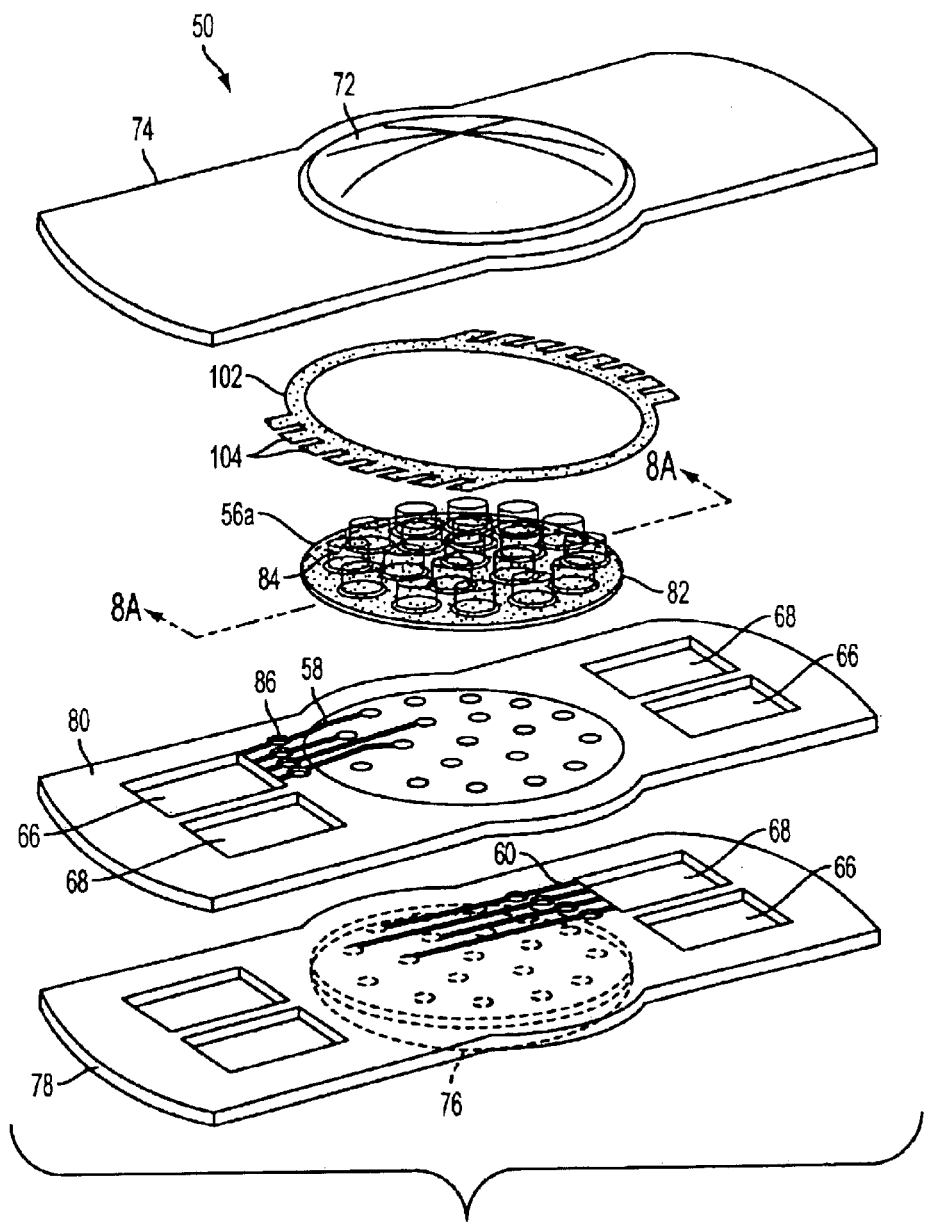
FIGS. 7A and 7B are, respectively, exploded perspective and side sectional views of the intraocular lens of FIGS. 6A and 6B.

Referring to FIGS. 6A, 6B and 7A, an alternative embodiment of an intraocular lens in accordance with the present invention is described in which laser-actuable valves are provided as the flow control mechanism. Lens 50 includes optic portion 52 and non-optic or haptic portion 54 for engaging the lens capsule as when used in an in-the-capsule implant following cataract surgery. Non-optic portion 54 in the IOL of FIG. 1 comprises a plate-type haptic but alternatively may comprise any type of arm-type haptics as described above with respect to the embodiment of FIGS. 1–5.

The flow control mechanisms employed in this embodiment are shown schematically in FIG. 6B, and are described seriatim. Optic portion 52 of lens 50 includes a plurality of fluid-filled chambers or cells 56a, 56b, . . . 56n within an interior portion of the lens that are fabricated from a resilient polymeric material known in the art of IOL fabrication. Illustratively, lens 50 is shown having 19 such cells, although the actual number of cells may range between 1 and about 250.

Each cell 56a . . . 56n is coupled to fluid inflow channel 58 and outflow channel 60, and the interior of each cell is coupled to its corresponding inflow and outflow channels by valves 62 and 64, respectively. Valves 62 and 64 are targetable and adapted for actuation by a laser source. Each inflow channel 58 and outflow channel 60 is coupled to first and second reservoirs 66 and 68, respectively, disposed in haptic portion 54.

In one embodiment reservoir 66 comprises a positive pressure supply reservoir relative to the pressure within fluid-filled cells 56a . . . 56n and reservoir 68 comprises a negative pressure reservoir or sink reservoir relative to the pressure within cells 56a . . . 56n. In an alternative embodiment, micropumps may be provided in fluid communication with the first and second reservoirs and fluid-filled cells.

Reservoirs 66 and 68, each of which may be plural in number as shown in FIGS. 6A and 6B, communicate with the inflow and outflow channels 58 and 60, respectively. In general, referring to FIG. 6B, fluid 70 may be controlled to flow into cells 56a . . . 56n from reservoirs 66 by way of inflow channels 58 to alter the curvature of central optic portion 72 of an anterior element 74 of the lens (see FIG. 7A). Fluid 70 also may be moved out of cells 56a . . . 56n to reservoir 68 by way of outflow channels 60 to reverse any curvature changed in the central optic portion 72.

The components of lens 50 preferably are fabricated from a somewhat flexible polymer such as silicone, hydrophobic or hydrophilic acrylic, hydrogel, collamer or other polymer with any suitable index of refraction, as is known in the art. The combination of components all are of similar materials with a similar index, and may be assembled to provide a typical bi-convex lens or a plano-convex or concavo-convex lens. In this respect, the lens may be substantially thin as in a contact lens.

Figure 7B:
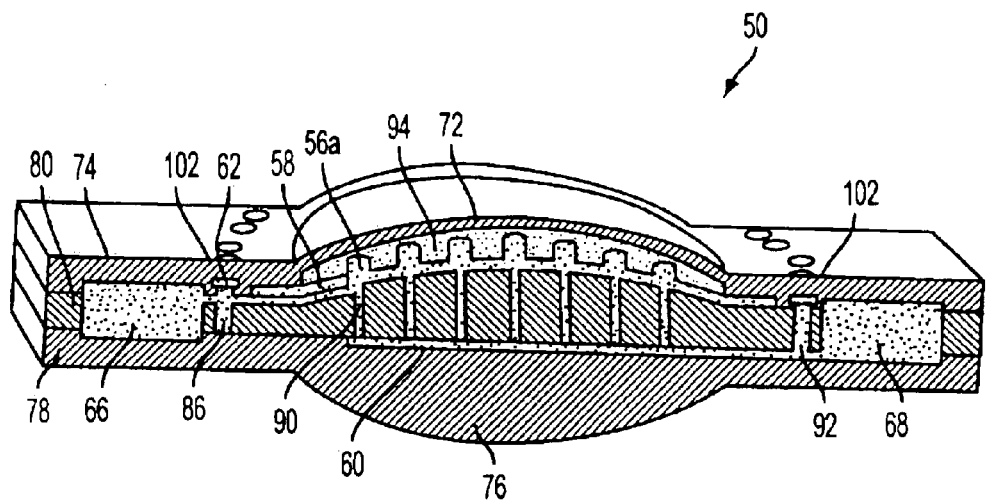

In FIGS. 7A and 7B, lens 50 has a bi-convex optic portion wherein anterior surface 72 has anterior curvature AC and posterior surface 76. The exploded view of FIG. 7A illustrates that lens 50 is assembled from anterior body element 74 and posterior body element 78 together with at least one intermediate body element 80. Each of body elements 74, 78 and 80 is molded from a silicone or similar material as described above.

In the embodiment of FIGS. 7A and 7B, intermediate body element 80 carries inflow channels 58 molded therein, while outflow channels 60 are shown as being molded into an interior surface of posterior body element 78. It should be appreciated that the plurality of inflow and outflow channels may be molded into intermediate element 80 and/or any of the other interior surfaces of the anterior, intermediate or posterior body elements 74, 78 and 80. The interior of the lens body further includes an independent molded cell component 82 that carries the plurality of cells 56a . . . 56n within molded structures 84.

Inflow reservoirs 66 and outflow reservoir(s) 68 also are molded into the interior of the lens, with reservoir cavity portions 66 and 68 extending into one or more of body elements 74, 78 and 80. Intermediate body element 80 also carries molded valve seats 86 that are adapted to cooperate with photothermally responsive nickel titanium alloy valve component 102, described herein below. The valve seats 86 alternatively may be molded into one of more of the anterior, posterior and intermediate body elements 74, 78 or 80.

It should be appreciated that the number of independent molded components of the lens may number from 2 to about 6, and that a variety of designs are possible for molding the plurality of cells 56a . . . 56n, inflow and outflow channels 58 and 60, reservoirs and valve seats in the lens body, all of which fall within the scope of the invention.

Recent advances in microfluidics, so-called "soft" lithography and micro-molding make a lens of the type depicted in FIG. 7A feasible with micron-scale features. Accordingly, it should be appreciated that the views of FIGS. 7A and 7B are provided to allow an understanding of the principles of operation of lens, are not-to-scale, and that the actual features of the inventive lenses may range in dimension from about 1 micron to 100 microns. For example, one company that has developed technology in die microfluidics fabrication field is Fluidigm Corporation, 7100 Shoreline Court, South San Francisco, Calif. 94080.

Fluidigm Corporation has developed technologies for forming and fabricating micron-scale channels, pumps, microvalves and other three-dimensional structures in multiple layers of soft polymers that function as fluidic circuitry. Multiple layers may be imprinted with the desired features and irreversibly bonded to one another by polymerization processes to provide a unitary lens body that has a uniform index of refraction. The fluid 70 that is provided within the fluidic circuitry of the lens may be a selected silicone fluid with a matching index of refraction.

A number of the technologies that enable the microfluidic elements of the present invention were developed at the California Institute of Technology in the 1990s. The following papers and materials are all incorporated herein by reference and describe fabrication techniques, components and aspects of microfluidics in soft polymers such as can be used to fabricate the lens of the present invention: S. R. Quake and A. Scherer, "From Micro to Nano Fabrication with Soft Materials", Science 290: 1536–40 (2000); P. Chou, M. A. Unger, and S. R. Quake, "A Microfabricated Rotary Pump", Biomedical Microdevices 3:323–330 (2001); M. A. Unger, H.-P. Chou, T. Thorsen, A. Scherer, and S. R. Quake, "Monolithic Microfabricated Valves and Pumps by Multilayer Soft Lithography", Science 288: 113–116 (2000); H. P. Chou, M. A. Unger, A. Scherer and S. R. Quake, "Integrated Elastomer Fluidic Lab on a Chip-Surface Patterning and DNA diagnostics", in Proceedings of the Solid State Actuator and Sensor Workshop, Hilton Head, S.C. (2000); H. P. Chou, C. Spence, A. Scherer and S. Quake, "A Microfabricated Device for Sizing and Sorting DNA Molecules", Proc. Nat'l Acad. Sci. 96: 11–13 (1999); A. Y. Fu, H. P. Chou, C. Spence, F. H. Arnold and S. R. Quake, "An Integrated Microfabricated Cell Sorter, Anal. Chem. (2002); and T. Thorsen, R. W. Roberts, F. H. Arnold and S. R. Quake, "Dynamic Pattern Formation in a Vesicle-Generating Microfluidic Device", Phys. Rev. Lett, 86: 4163–6 (2001).

Referring now to FIG. 7B, a sectional view of the assembled components 74, 78 and 80 is shown, where the section passes through several cells (e.g., 56a . . . 56n) that alter the anterior curvature AC of the lens. In this embodiment, positive pressure reservoir 66 is coupled by inflow channel 58 to chamber 56a. Inflow channel 58 is formed in an upper surface of intermediate element 80 that extends from reservoir 66 through inflow valve seat 86 and terminates at the base of fluid-filled cell 56a. Outflow channel 60 is defined in part by bore 90 through intermediate element 80 and further extends along an upper surface of posterior element 78 (and outflow valve seat 92) to the negative pressure reservoir 68. The lens assembly further defines space 94 about an exterior of the cell component 82 and the interior of central portion 72 of anterior body element 74. Space 94 is filled with index-matched fluid 70.

Figure 8A:
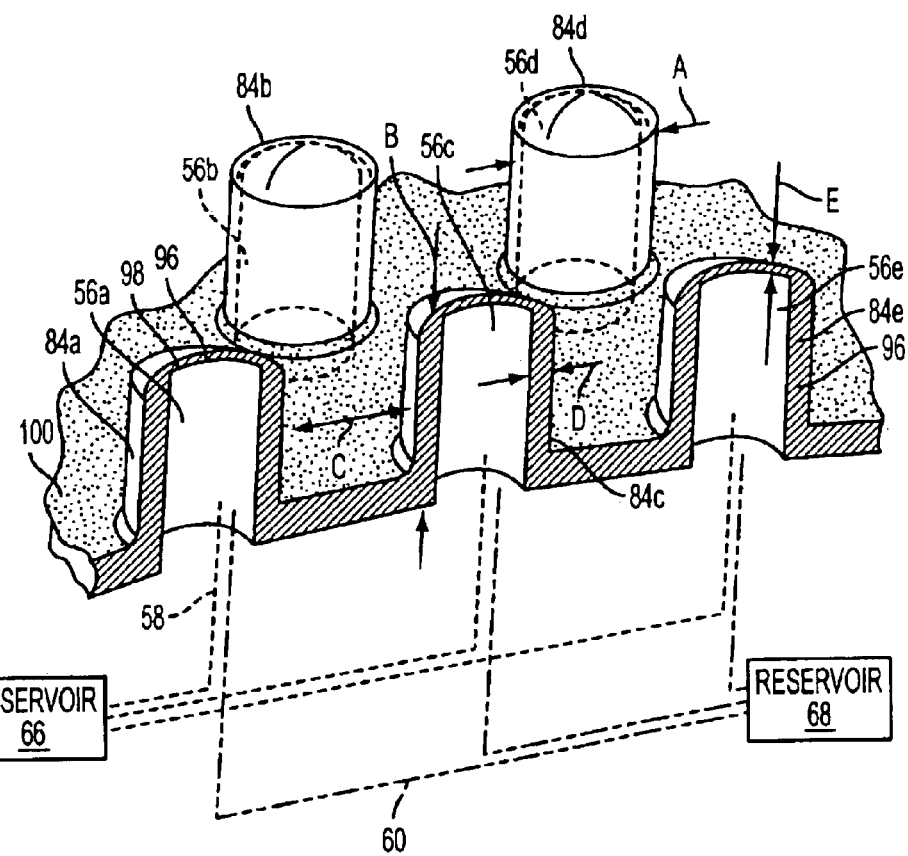
FIGS. 8A and 8B are detailed partial sectional perspective views of the deformable cells of the lens of FIGS. 6 and 7 depicting selective actuation of the deformable cells.
Figure 8B:
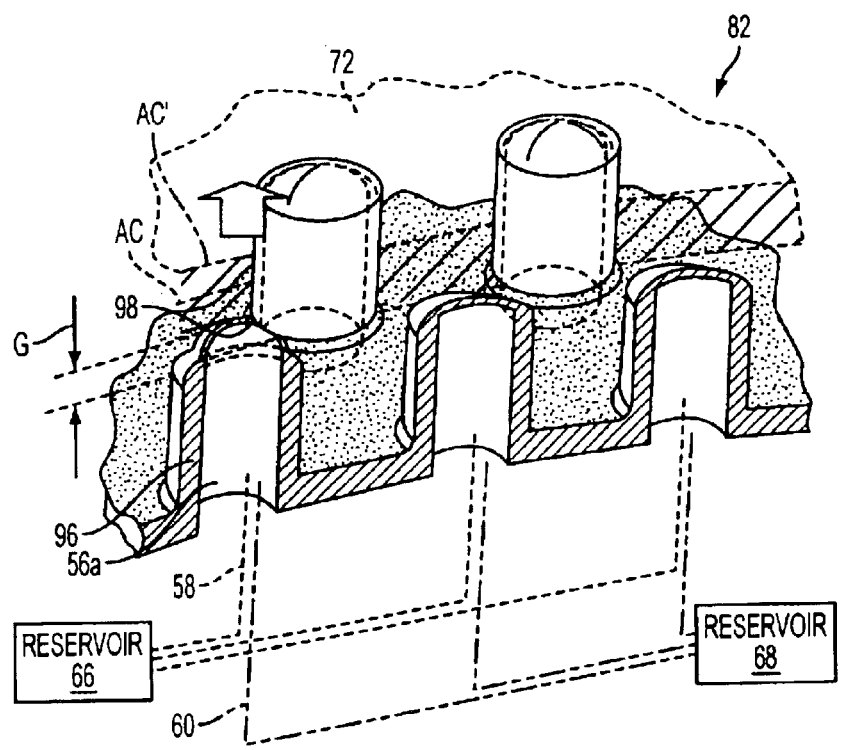

Turning now to FIGS. 8A and 8B, an enlarged view of a portion of cell component 82 is provided to illustrate its method of use as well a methods of fabricating the component. Cell component 82 carries a plurality of cells 56a, 56b, 56c, 56d and 56e within molded structures 84a–84e. In general, as described above, the number of molded structures may range from 1 to about 200, and preferably is from about 20 to 120. Molded structures 84a . . . 84e extend generally orthogonal to the plane of intermediate element 80 (see FIG. 7B) and are aligned with the optical axis of lens 50. Each molded structure 84a . . . 84e defines an exterior wall portion 96 and a substantially elastic deformable anterior wall portion indicated at 98 for engaging, deforming and adjusting the anterior lens surface. The base portion 100 of component 82 is adapted for bonding to an anterior surface of body element 80.

Molded structures 84a . . . 84e and cells 56a . . . 56e therein may have any suitable dimensions and spacing therebetween. For example, dimension A represents a diameter of an exemplary structure 84d that may range between about 20 microns and 5 mm. The height of the structure 56c indicated at dimension B ranges between about 10 microns and 100 microns. The spacing C between the structures 56a and 56b may range between about 0 microns and 1000 microns. The thickness D of the exterior side walls 98 of the molded structures may range between about 10 microns and 200 microns.

The molded structures may vary in dimension, and in one embodiment the more centrally located structures may be larger or more spaced apart than the more peripheral molded structures. The molded structures may have any shape such as cylindrical, tapered, conical, hexagonal, etc. In a typical embodiment, the exterior wall portion 98 of each molded structure has a substantial thickness to prevent radial expansion of the structure and the cell therein when the volume of fluid 70 therein is increased in volume.

As may be seen by comparing FIGS. 8A and 8B, an inflow of fluid 70 into the cell 56a expands the thin-wall anterior portion 98 a selected dimension indicated at G. This expansion of thin anterior wall 98 that bounds cell 56a engages and pushes anteriorly the resilient central optic portion 72 of anterior element 74. Anterior wall 98 of molded structure 84a . . . 84e may range in thickness E from about 1 micron to 40 microns, and more preferably from about 2 microns to 20 microns. The amplitude G of movement of anterior wall 98 of each structure 84a . . . 84e may range from about 1 micron to 100 microns or more.

Expansion of cell 56a deforms and alters the anterior curvature AC of the lens to AC'. As will be understood from FIGS. 8A and 8B, lens 50 of the present invention provides for the correction of defocus error as well as other aberrations by the activation and axial displacement central optic portion 72 of anterior element 74 of the lens at or about several localized paths. The cells 56a . . . 56n underlying the targeted locations are altered in dimension by fluid flows, wherein the effect is to increase or decrease the optical path of light through the altered portion of the lens.

In accordance with the principles of the present invention, each of several areas of the central optic portion of the lens may be modified, either increasing or decreasing the optical path traversing the IOL in the altered lens portion. The optical aperture or lens surface thus may be separated into multiple individually addressable regions, with each molded structure capable of altering the anterior curvature AC in a dimension substantially axial to the optic axis of the IOL. Each element may be actuated through the addition of, or subtraction of, fluid media 70 from the dimensionally-alterable cells 56a . . . 56n.

As discussed above for the embodiment of FIGS. 1–5, it is important that the individual molded structures 84 and the corresponding cells act in unison so that no discontinuities exist between adjacent cells. The system of spaced apart deformable molded structures allows the system to create substantially smooth radii of curvature in the anterior lens surface, which is a function of, and controlled by, the cross-section A of the molded structures 84 and cells 56a . . . 56n, the spaced apart dimension C between the molded structures and the thickness, durometer and other physical properties of the central optic portion 72 of the anterior element 74.

Space 94 between molded structures 84 and the interior surface of wall 72 of the anterior lens element 74 contains the same index-matched fluid as is used in the fluid circuitry of the lens. Fluid 70 is selected such that it is index-matched to molded structures 84 of and adjoining surfaces that might otherwise cause unwanted phase errors or diffractive effects.

Figure 9A:
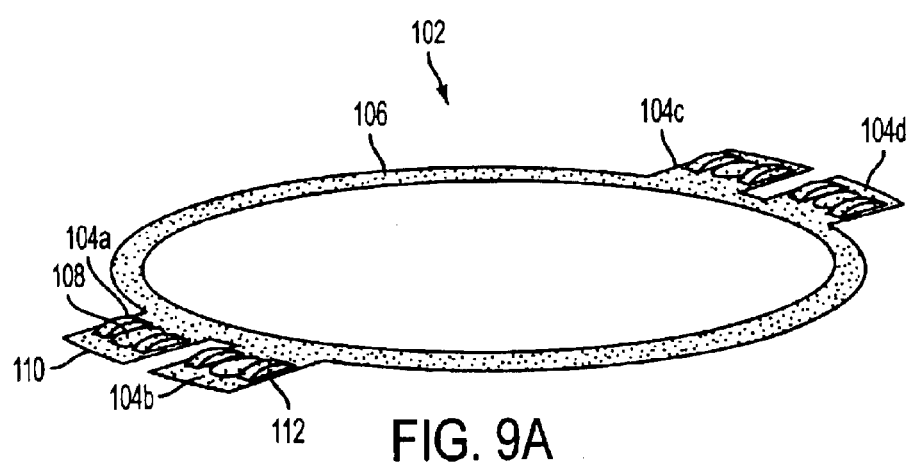
FIGS. 9A and 9B are, respectively, a perspective and enlarged partial perspective isolation view of a thin-film nickel titanium alloy member, similar to that of FIGS. 6A and 6B (de-mated from the lens body) illustrating a photo-thermally responsive shape memory alloy component of an exemplary valve.
Figure 9B:
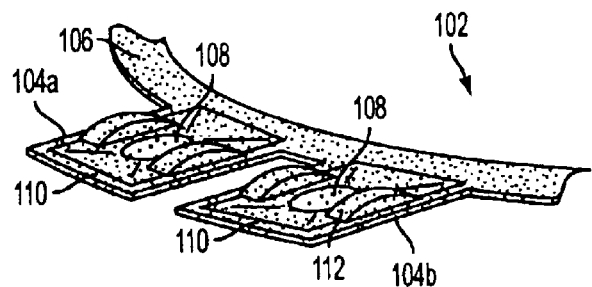

Referring now to FIGS. 9A and 9B, an exemplary valve system and methods are described for controlling the flow of fluid 70 into and out of the cells 56a . . . 56n and reservoirs 66 and 68. Various types of microvalves have been developed that are responsive to application of energy from a remote source, any one of which may be used in the lens according to the invention. The exemplary valve system described herein is based on thin-film shape memory alloy (SMA) materials that actuate a valve diaphragm in response to a photothermal effect. Thus, the lens can be easily adapted to cooperate with a low power laser, galvanometric scanning system, and optional laser tracking system, all known on the art of laser refractive technologies, to target and actuate one or more valve mechanisms carried in lens 50.

Referring also to FIGS. 7A and 7B, the intermediate region of lens 50 carries an annular member 102 of a thin-film nickel titanium (Nitinol) shape memory alloy. In general, the use of thin-film fabrication methods allow a single component to provide the diaphragm portions of the plurality of inflow and outflow valves that enable the operation of the lens.

As is well known, a nickel titanium alloy may be annealed so that it crystallizes in a manner that exhibits shape memory properties, a property that has found use in a number of medical implants such as endovascular stents. Virtually all uses of nickel titanium alloys have been developed from bulk materials in sheet or tubular forms. While various methods have been developed to draw tubes or to roll sheets of SMAs, conventional methods may be used to fabricate thin films in the 2 to 20 micron range needed for the invention.

Recently, techniques have been developed for sputter-deposited materials to provide thin film SMA materials, as well as to allow fabrication of MEMS components. Sputter-deposited thin film SMAs alloys such as nickel titanium films can be fabricated in a range of thickness from less than 1 micron to about 25 microns. The following papers describe methods of sputter-depositing thin films and annealing the SMA materials, which are incorporated herein by reference: V. Gupta, A. D. Johnson, V. Martynov, V. Galhotra, Thin Film Shape Memory Alloy for Medical Applications, Nano-Space 2000, an international micro/nano technology conference, Houston, Tex. Jan. 23–28, 2000; P. Krulevitch, A. P. Lee, P. B. Ramsey, J. C. Trevino, J. Hamilton, M. A.

Northrup, Thin film Shape Memory Alloy Microactuators, J. Micromech. Microeng. Vol. 5, No. Dec. 4, 1996; A. David Johnson and Erik J. Shahoian, "Recent Progress in Thin Film Shape Memory Microactuators," MEMS '95, Proceedings IEEE Micro Electro Mechanical Systems, p. 216 (1995); S. Z Hua, C. M. Su, M. Wuttig, "Transformation Induced Stress in SMA Thin Films", MRS Symp. Proc. on Thin Films Stress and Mechanical Properties, 308, 525 (1993), and A. D. Johnson, Vacuum-Deposited TiNi Shape memory Film: Characterization and Applications in Micro-Devices, J. Micromech. Microeng. Vol.1, (1991) 34–41.

For use as a micro-valve, the SMA material is annealed into a crystalline state wherein it undergoes a crystalline phase transformation from martensite to austenite when heated through the material's phase change transformation temperature. When below that temperature the material can be plastically deformed from a "memory shape" responsive to stress. When the SMA material is heated through the transformation temperature, it forcefully reverts to its memory shape, at the same time exerting considerable force.

In one lens embodiment, each cell, such as chamber 56a in FIG. 8B has two associated valves 58 and 60 for controlling inflows and outflows of fluid 70. It is desirable to limit the number of component parts and for this reason a micro-machined nickel titanium alloy valve mechanism may be best suited for the inventive lens. For convenience, the annular SMA member in FIG. 9A shows only four not-to-scale valve diaphragm portions 104a–104d that extend away from annular portion 106. It will be appreciated that the number of diaphragm portions 104a–104d may be increased to any number needed for the invention.

FIG. 9B shows an enlarged view of the SMA valve diaphragm portions 104a and 104b that define a non-planar form 108 that extends away from planar edges portions 110 and planar annular portion 106. Each non-planar form 108 is shown with an optional spring element 112 formed therein to assist in urging the valve to a closed position. The center of non-planar form 108 also optionally may be coated with a light-absorbing composition that cooperates with a selected wavelength of light.

Figure 10A:
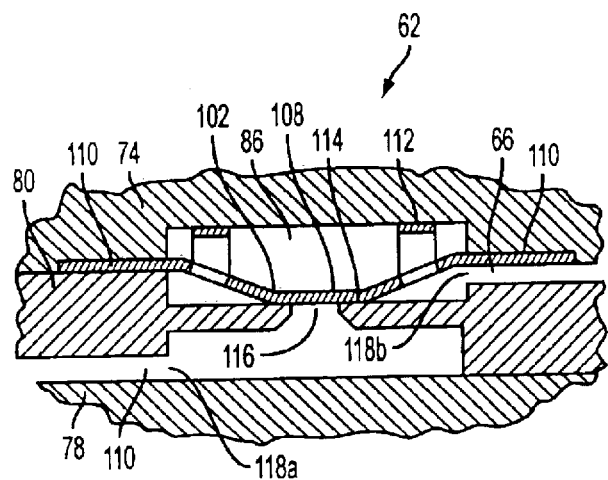
FIGS. 10A and 10B are, respectively, schematic sectional views of the thin-film nickel titanium alloy component of FIGS. 9A and 9B, after insert molding into the lens body, showing the normally closed and open positions of the valve.
Figure 10B:
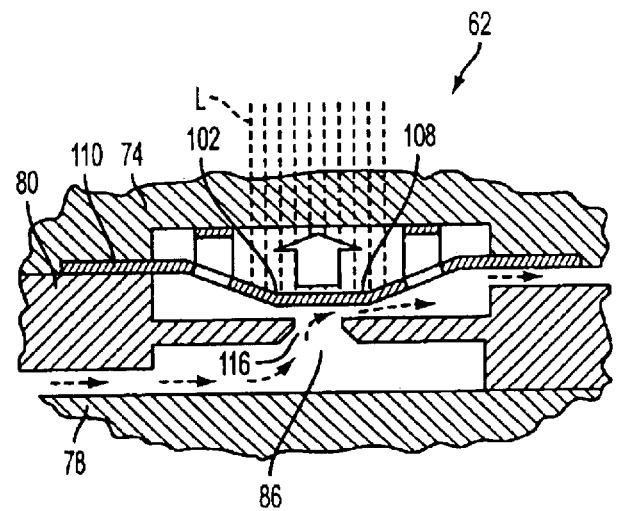

Referring now to FIGS. 10A and 10B, the operation of a thermo-responsive valve 62 is described. FIG. 10A is a sectional view of valve 62 showing that planar edge portions 110 are sandwiched between a posterior surface of anterior element 74 and anterior surface of intermediate element 80. The non-planar SMA portion 108 of the member is carried in an open cavity or valve seat 86 of the lens body assembly. At rest, valve 62 is in a normally closed position with the non-planar SMA portion 108 pressed against valve seat 114 and closing off aperture 116. Inflow channel 58 (see FIG. 6B) is shown in FIG. 10A with first portion 118a entering valve cavity 86 and a second portion 118b exiting the valve cavity on the opposite side of closed-off aperture 116.

FIG. 10B shows valve 62 moved to an open position by the photothermal targeting. A laser beam indicated at L is directed to impinge on the non-planar form 108 of the valve. The increase in temperature of the non-planar form 108 causes the SMA to alter its dimension across the thin film expanse and lift away from the valve seat 116 to thereby open the valve. As indicated by the arrows in FIG. 10B, fluid then flows from the reservoir to a cell, or from a cell to the sink reservoir. The method of utilizing an SMA member to move between first and second shapes to open and close a valve extends to similar systems wherein the SMA member is adapted to impinge on a collapsible lumen to terminate fluid flows or to open a collapsible lumen, all of which are known in the art.

As for the embodiment of FIGS. 1–5, the net effect of modifying fluid volume in cells 56a . . . 56n, each and in concert, is to improve the optical performance of the lens system. By the proper choice of the extent of displacement of cells 56a . . . 56n, either increasing the OPD or decreasing it, the IOL may be made to cancel all or a substantial portion of the optical imperfection associated imaging system. Thus, an incoming wavefront from the cornea will impinge upon the IOL, and the aberrated wavefront can be substantially compared to ideal spherical wavefront. The individual cells then may be modified to impart the appropriate OPD upon the wavefront such that the wavefront is substantially perfect after transmission through the lens.

The lens of the present invention, when used as an intraocular implant, may be coupled with a diagnostic instrument such as a Shack Hartman wavefront sensing system or any other type of wavefront sensor to provide real-time intraoperative feedback of the adjusted optical parameters of the lens. By this means, the lens may be optimized to correct both spherically and for higher order aberrations.

Although the lens embodiment of FIGS. 6–10 provided inflow valve 62 and outflow valve 64 for each inflow channel 58 and outflow channel 60, it will be appreciated that the discrete number of valve mechanisms in a lens may be reduced in number by using a manifold that is coupled to each fluid-filled cell by a single inflow-outflow channel, wherein the manifold may be switched between being fluidly coupled to either a positive pressure or negative pressure pump or reservoir.

Those skilled in the art will appreciate that the exemplary embodiments and descriptions thereof are merely illustrative of the invention as a whole, and the present invention is not limited to the specific embodiments described herein. Specific features of the invention may be shown in some figures and not in others, and this is for convenience only and any feature may be combined with another in accordance with the invention. While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A lens comprising:
   a lens portion defining an anterior surface layer and a posterior surface layer;
   an interior of the lens portion comprising an array of deformable cells each defining a volume of a selected fluid therein, each deformable cell in substantial engagement with either the anterior or posterior surface layer;
   means for controllably causing fluid flow to alter the volume in at least a portion of the array of deformable cells to thereby controllably deform the anterior or posterior surface layer and alter optical parameters of the lens.

2. The lens of claim 1 wherein the array of deformable cells defines an axis that is substantially perpendicular to the anterior or posterior surface layer.

3. The lens of claim 1 wherein the array of deformable cells comprises hexagonal cells.

4. The lens of claim 1 wherein the array of deformable cells comprises round cells.

5. The lens of claim 1 wherein the means for controllably causing fluid flow to alter the volume in at least a portion of the array of deformable cells comprises a reservoir communicating with each cell via a channel, and a flow control mechanism for controlling movement of fluid between the deformable cell and the reservoir.

6. The lens of claim 1 wherein a single reservoir communicates with a subset of the array of deformable cells.

7. The lens of claim 5 wherein the flow control mechanism comprises a sacrificial plug.

8. The lens of claim 5 wherein the flow control mechanism comprises a valve operatively connected to each channel.

9. The lens of claim 8 wherein the valve is a photo-activated valve.

10. The lens of claim 5 wherein the reservoir is located within a periphery of the lens.

11. A power adjustable lens for vision correction, comprising:

a resilient lens body defining an anterior curvature and a posterior curvature;

an interior portion of the lens body including an array of deformable fluid-filled structures that engage a surface element of the lens body;

means for controllably causing a fluid to flow into or out of each fluid-filled structure to thereby controllably deform and alter an optical parameter of the lens.

12. The lens of claim 11 wherein the means for controllably causing a fluid to flow into or out of each fluid-filled structure comprises:

first and second reservoirs in communication with an interior chamber of each fluid-filled structure via respective first and second channels; and a valve system coupled to said first and second channels for controlling fluid flows to the interior chamber of each fluid-filled structure.

13. The lens of claim 12 wherein the first reservoir defines a high internal fluid pressure relative to each fluid-filled structure and the second reservoir defines a low internal fluid pressure relative to each fluid-filled structure.

14. The lens of claim 12 wherein the valve system is normally closed and is openable by application of energy from an external source.

15. The lens of claim 12 wherein the valve system is photo-thermally actuated.

16. The lens of claim 12 wherein the valve system includes micro-actuator of a shape memory alloy.

17. The lens of claim 11 wherein the body of the fluid-filled structures and the fluid have matching indices of refraction.

18. The lens of claim 11 wherein the fluid-filled structures define a deformable engagement portion that engages a deformable surface element of the lens.

19. A method of adjusting the power of a lens used in vision correction, comprising:

providing a lens body with a plurality of deformable fluid-filled structures in an interior of the lens that engage a surface element of the lens body; and controllably altering the volume of the fluid within selected fluid-filled structures thereby deforming the fluid-filled structure and the engaged surface element to thereby alter an optical parameter of the lens.

20. The method of claim 19 further comprising providing an index-matched fluid in a space in the lens body interior of the surface element and exterior of the deformable fluid-filled structures.

21. The method of claim 19 wherein controllably altering the volume of the fluid within selected fluid-filled structures includes actuating a valve system with light energy from an external source.

22. The method of claim 19 wherein controllably altering the volume of the fluid within selected fluid-filled structures comprises actuating at least one valve from a normally closed position to an open position with light energy from an external source.

23. The method according to claim 19 wherein controllably altering the volume of the fluid within selected fluid-filled structures comprises actuating at least one valve from a normally open position to a closed position with light energy from an external source.

24. The method of claim 19 wherein controllably altering the volume of the fluid within selected fluid-filled structures further comprises:

providing a wavefront sensing system; and contemporaneously calculating optical parameters of the lens.

25. The method of claim 19 further comprising polymerizing the fluid to a substantially solid state to permanently fix the optical parameters of the lens.

26. A power adjustable lens for vision correction, comprising:

a lens body defining a resilient anterior surface element and a optical axis;

one or more resilient structures, each resilient structure having a fluid-filled interior chamber therein and extendable relative to optical axis between a first retracted position and a second extended position;

a reservoir; and flow control means for causing flow of an index-matching fluid into or out of each resilient structure to deform the resilient anterior surface element and alter an optical parameter of the lens.

27. The lens of claim 26 wherein the resilient structures range in number between 1 and 500.

28. The lens of claim 26 wherein the resilient structures have a cross section ranging between about 20 microns and 5 mm.

29. The lens of claim 26 wherein the resilient structures define a dynamic range between the first retracted position and a second extended position between about 1 microns and 100 microns.

* * * * *